United States Patent
Palmer

(10) Patent No.: US 10,751,213 B2
(45) Date of Patent: *Aug. 25, 2020

(54) DUAL-PURPOSE URINARY CATHETER DRAIN LINE AND COLLECTION BAG

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/740,865

(22) Filed: Jan. 13, 2020

(65) Prior Publication Data

US 2020/0146871 A1 May 14, 2020

Related U.S. Application Data

(63) Continuation-in-part of application No. 16/352,538, filed on Mar. 13, 2019, now Pat. No. 10,531,976, which is a continuation of application No. 15/956,561, filed on Apr. 18, 2018, now abandoned.

(51) Int. Cl.
*A61F 5/44* (2006.01)
*A61M 25/00* (2006.01)

(52) U.S. Cl.
CPC ....... *A61F 5/4404* (2013.01); *A61M 25/0017* (2013.01); *A61M 2025/0018* (2013.01); *A61M 2025/0062* (2013.01); *A61M 2202/0496* (2013.01); *A61M 2210/1085* (2013.01); *A61M 2210/1089* (2013.01)

(58) Field of Classification Search
None
See application file for complete search history.

(56) References Cited

U.S. PATENT DOCUMENTS

| | | | |
|---|---|---|---|
| 3,699,964 A | 10/1972 | Ericson | |
| 4,230,115 A * | 10/1980 | Walz, Jr. | ............. A61M 1/0019 604/517 |
| 4,246,909 A | 1/1981 | Wu et al. | |
| 5,087,251 A | 2/1992 | Heyman et al. | |
| 5,454,798 A | 10/1995 | Kubalak et al. | |
| 5,582,165 A * | 12/1996 | Bryan | ............... A61M 16/0488 128/207.14 |
| 6,053,905 A | 4/2000 | Daignault et al. | |

(Continued)

*Primary Examiner* — Adam Marcetich
(74) *Attorney, Agent, or Firm* — SoCal IP Law Group LLP; Guy Cumberbatch; Steven Sereboff

(57) ABSTRACT

A sterile dual-purpose closed intermittent urinary catheter system that may be used as either a drain line or a collection bag. A catheter resides within an inner cavity of an extensible sheath and may be extracted from a forward end through an outlet hub for insertion into the urethra. A valve at a rearward end of the sheath may be opened to permit the sheath to function as a drain line, or closed to permit the sheath to function as a collection bag. The sheath has an extended length substantially longer than the catheter length, and may be compressed in an accordion fashion or folded to a compact packaged shape. The urine may be collected in the sheath with the valve closed, or drained straight into a toilet with the valve open. The system may have a source of lubrication to wet the catheter.

20 Claims, 5 Drawing Sheets

(56) References Cited

U.S. PATENT DOCUMENTS

| | | | |
|---|---|---|---|
| 6,090,075 A | 7/2000 | House | |
| 6,578,709 B1 | 6/2003 | Kavahagh et al. | |
| 6,849,070 B1* | 2/2005 | Hansen | A61F 5/44 604/328 |
| 7,601,158 B2 | 10/2009 | House | |
| 7,918,831 B2 | 4/2011 | House | |
| 7,938,838 B2 | 5/2011 | House | |
| 8,177,774 B2 | 5/2012 | House | |
| 8,317,775 B2 | 11/2012 | House | |
| 8,771,286 B2 | 7/2014 | House | |
| 8,845,620 B2 | 9/2014 | House | |
| 2002/0103467 A1 | 8/2002 | Kubalak | |
| 2003/0018302 A1 | 1/2003 | Kavabagh et al. | |
| 2004/0171979 A1 | 9/2004 | O'Neil | |
| 2005/0011789 A1 | 1/2005 | Tsaur | |
| 2006/0025753 A1 | 2/2006 | Kubalak et al. | |
| 2007/0057222 A1 | 3/2007 | Iverson | |
| 2007/0161971 A1* | 7/2007 | House | A61M 25/0111 604/544 |
| 2008/0051763 A1 | 2/2008 | Frojd | |
| 2008/0119803 A1* | 5/2008 | Lund | A61M 27/008 604/327 |
| 2008/0172016 A1* | 7/2008 | House | A61F 5/44 604/317 |
| 2009/0000970 A1* | 1/2009 | Bordeau | A61M 25/0111 206/364 |
| 2009/0062755 A1 | 3/2009 | Burgess et al. | |
| 2009/0163884 A1 | 6/2009 | Kull-Osterlin et al. | |
| 2009/0204106 A1 | 8/2009 | Golden | |
| 2011/0030130 A1 | 2/2011 | Stein | |
| 2012/0184944 A1 | 7/2012 | Tomes et al. | |
| 2013/0161227 A1* | 6/2013 | Gustavsson | A61M 25/002 206/571 |
| 2014/0180260 A1 | 6/2014 | Muller | |
| 2015/0000023 A1 | 1/2015 | Massey | |
| 2015/0000024 A1 | 1/2015 | Plath | |
| 2015/0105756 A1* | 4/2015 | O'Brien | A61M 25/0017 604/544 |
| 2015/0126975 A1 | 5/2015 | Wuthier | |
| 2015/0216754 A1* | 8/2015 | Cailleteau | A61G 9/006 4/144.2 |
| 2015/0250544 A1* | 9/2015 | Costargent | A61M 25/0111 248/49 |
| 2015/0306342 A1* | 10/2015 | Rostami | A61M 25/0045 604/544 |
| 2016/0120688 A1 | 5/2016 | Lee | |
| 2016/0193443 A1 | 7/2016 | Palmer | |
| 2017/0042724 A1 | 2/2017 | Ugarte | |
| 2018/0325720 A1* | 11/2018 | Brites Pinto | B65D 33/25 |
| 2019/0151610 A1 | 5/2019 | Fletter | |
| 2019/0321587 A1* | 10/2019 | McMenamin | A61F 5/44 |

\* cited by examiner

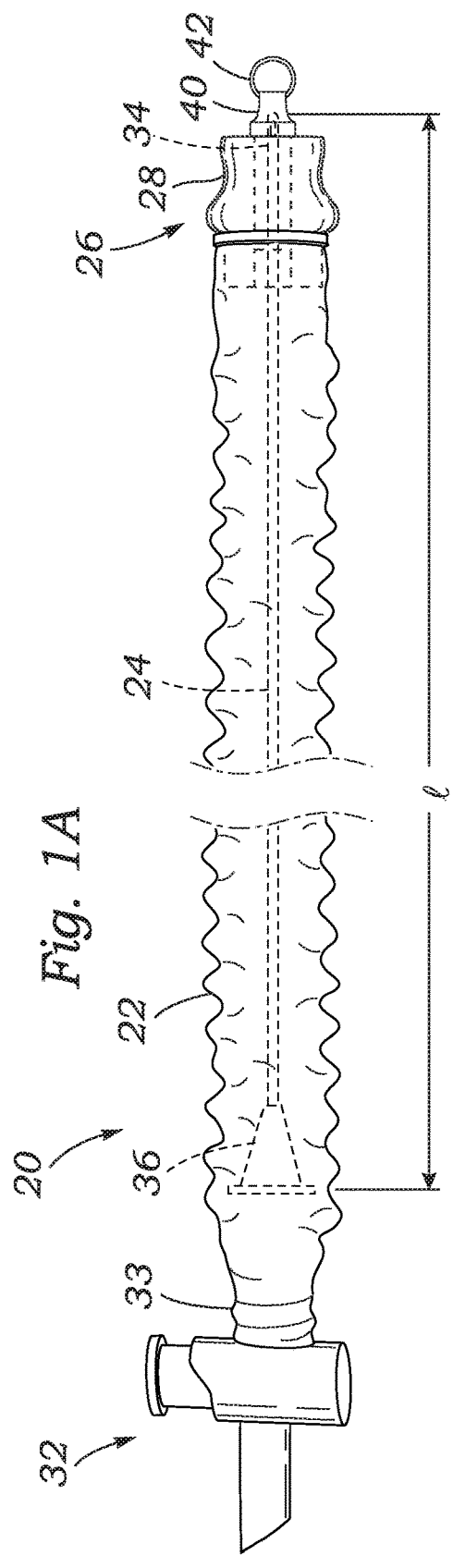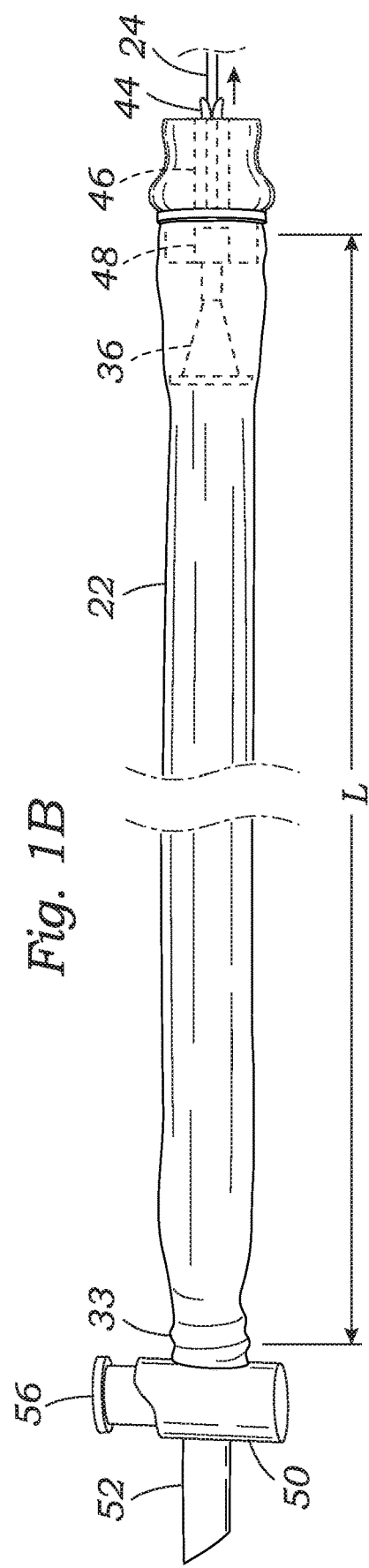

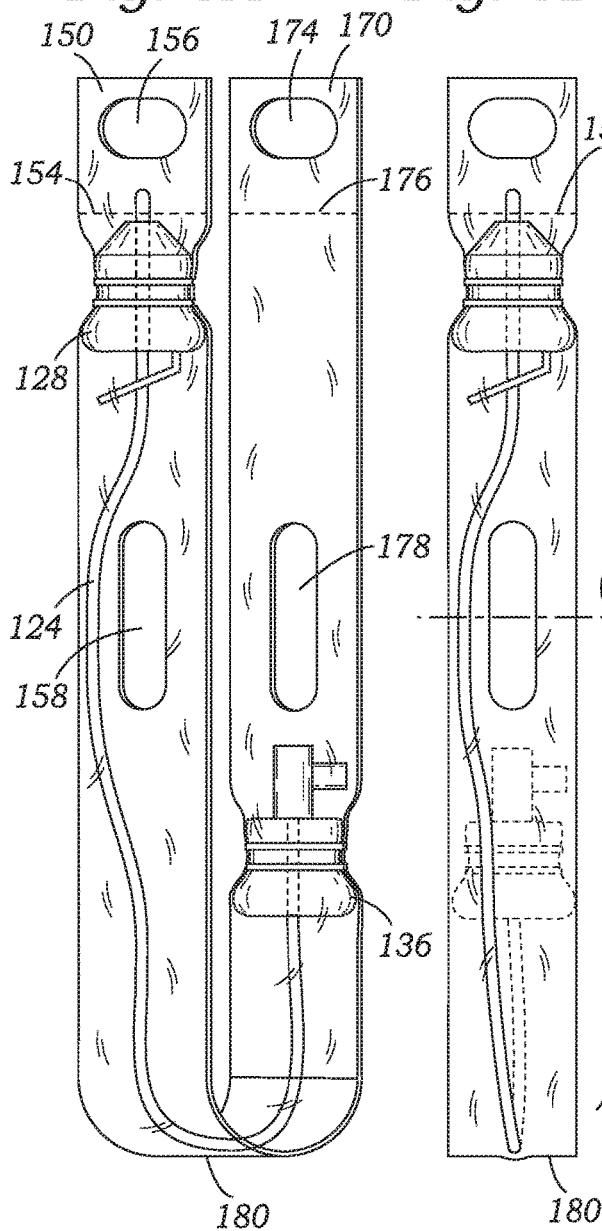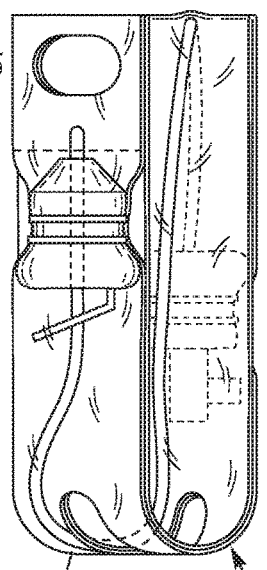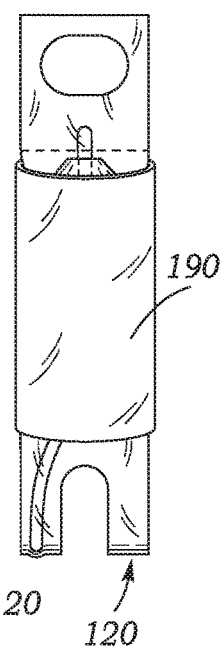

DUAL-PURPOSE URINARY CATHETER DRAIN LINE AND COLLECTION BAG

RELATED APPLICATIONS

This application is a continuation-in-part of U.S. patent application Ser. No. 16/352,538 filed Mar. 13, 2019, now issued as U.S. Pat. No. 10,531,976, which is a continuation of U.S. patent application Ser. No. 15/956,561 filed Apr. 18, 2018, the disclosures of which are expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present invention relates to an intermittent urinary catheter system and, more particularly, to a dual-purpose urinary catheter drain line and collection bag.

BACKGROUND

People with neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. But such continuous catheterization can lead to problems like urinary tract infections (UTI), urethral strictures or male infertility. Intermittent catheterization at regular intervals avoids such negative effects of continuous long term catheterization. Research has shown that intermittent self-catheterization helps reduce urinary tract infections, control urinary leakage (incontinence) and prevent urinary tract damage.

In our highly mobile culture, the ability to have the freedom to leave home for the day or longer is an important part of life. To accommodate this need, single use intermittent urinary catheters have been developed to allow patients to perform self-catheterization. Many intermittent catheters are designed to be inserted into the bladder while the back end is suspended over a toilet or other waste receptacle. For example, the mPower Cath Hydro hydrophilic intermittent urinary catheter available from Adapta Medical of Colorado Springs, Colo. provides a sterile catheter surrounded by an elongated flexible sheath. The catheter may be extracted from one end of the sheath, which collapses in pleats, for insertion in a urethra of a user. Urine drains through the catheter and flows out an opposite end outlet to be directed into either a toilet or a collection bag. Various aspects of such catheters may be seen in U.S. Pat. Nos. 6,090,075, 8,177,774 and 8,845,620.

On the other hand, a closed system catheter is a self-contained, sterile, pre-lubricated catheter housed within a collection bag. The collection bag eliminates the need to void the urine into a receptacle or toilet, and since it is self-contained, it eliminates the need to hook up any other kind of bag or container—it is truly portable.

Despite numerous products on the market, there remains a need for a more adaptable intermittent urinary catheter system.

SUMMARY OF THE INVENTION

The present application discloses a sterile dual-purpose intermittent urinary catheter system that may be used as either a drain line or a collection bag. In one embodiment, a catheter having a length resides within an inner cavity of an extensible sheath. The sheath is sealed at both ends and the catheter may be extracted from a forward end through a hub for insertion into the urethra. A valve at a rearward end of the sheath may be opened to permit the sheath to function as a drain line, or closed to permit the sheath to function as a collection bag. The sheath has an extended length substantially longer than the catheter length.

BRIEF DESCRIPTION OF THE DRAWINGS

FIG. 1A is an elevational view of an exemplary dual-purpose intermittent urinary catheter system with an outer sheath in a collapsed configuration with a catheter housed therein;

FIG. 1B is an elevational view of an exemplary catheter system with the outer sheath in a longitudinally extended configuration and the catheter partially withdrawn therefrom;

FIG. 5A is a perspective view of the catheter system of FIG. 4A folded in half, and FIG. 5B is an elevational view with the two folded halves flat against one another; and FIG. 6A is a perspective view of the catheter system of FIG. 4A folded in half again shown exploded from a tubular shipping seal, and FIG. 6B is an elevational view of the assembled twice folded catheter system and shipping seal.

DETAILED DESCRIPTION OF A PREFERRED EMBODIMENT

Figure 2:
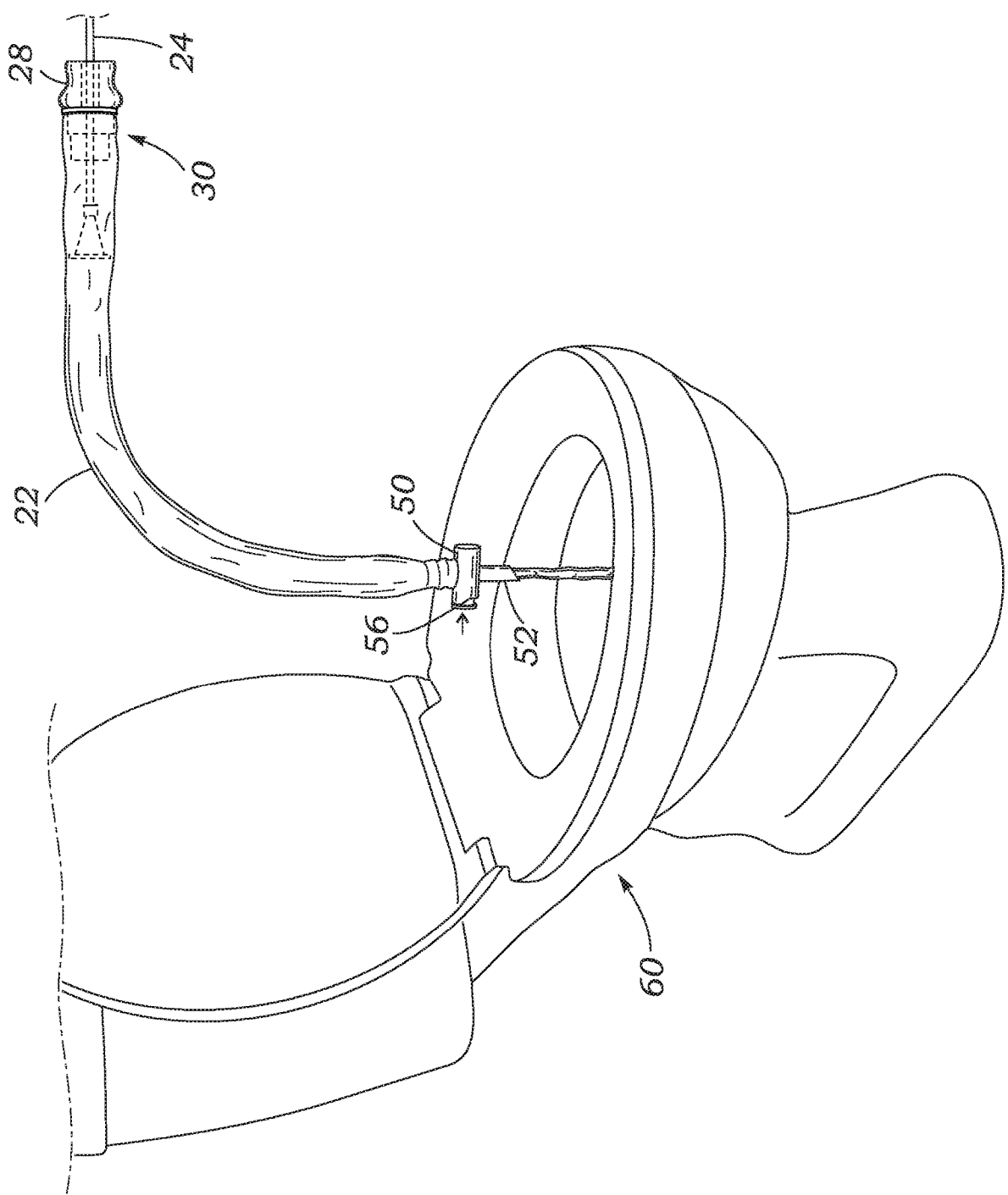
FIG. 2 is a perspective view of the system of the present application forming an open conduit and used as a drain line into a toilet.

The present application provides a closed system catheter which may be used in two ways and is thus dual-purpose. In a first mode of operation, the catheter provides a closed bag or sheath and a pre-lubricated catheter that may be extended therefrom. The user inserts the catheter into his or her urethra and thus may empty the bladder into the closed bag. In a second mode of operation, a back end of the bag may be opened so that the user can drain the flow into a convenient receptacle, such as a toilet. The bag is preferably highly extendible to provide a relatively long drain line. Conversion between the two modes is accomplished by actuating a valve incorporated into the bag.

FIG. 1A is an elevational view of an exemplary dual-purpose intermittent urinary catheter system 20 with a flexible, preferably transparent or at least translucent, outer sheath 22 and an elongated intermittent urinary catheter 24 disposed therein. The system 20 has a business or forward end 26 in the form of a rigid or semi-rigid outlet hub 28 that as shown is closed. A rearward end 32 includes a fluid valve which is also closed as shown and will be described in greater detail below.

In the storage and shipping configuration seen in FIG. 1A, opposite ends of the substantially tubular flexible outer sheath 22 are secured to the closed ends 26, 32 such as with heat sealing, adhesive, or a stricture 33 as seen at the rear end. Preferably, opposite ends of the outer sheath 22 are sized to closely surround both the outlet hub 28 and valve housing and are welded, adhered, heat shrunk or otherwise secured around the respective element. In its storage and shipping configuration, the flexible outer sheath 22 is collapsed or constricted longitudinally. The sheath 22 is desirably a thin polymer tube such as polyethylenes, polyamides (e.g., Nylon 11, nylon 12, nylon 6,6) polyurethanes, polyetherblockamides (e.g., PEBAX), polyesters and blends and compositions thereof which may be constricted longitudinally so as to form folds or pleats. Desirably, the outer sheath 22 has a diameter D of between 1-2 inches (2.54-5.08 cm), and a longitudinal dimension L of anywhere from 24-45 inches (61-114 cm).

The intermittent urinary catheter 24 extends from a forward tip 34 to a rear funnel or enlargement 36, and has a length $\ell$ which is less than the longitudinal dimension of the sheath 22, even when constricted. The catheter 24 is typically 14 or 16 inches in length, but may be less or more as desired. As the length $\ell$ of the catheter 24 is shorter than the length dimension of the sheath 22, the catheter is fully contained in a sterile manner within the sheath. Further, the assembly as shown in FIG. 1A is usually shipped in a larger outer package which displays product and instructional text, and may be easily opened and thrown away.

With reference to the forward end 26 of the system in FIGS. 1A and 1B, a sterile cap 40 with a pull ring 42 covers an opening on the front end of the outlet hub 28. Removal of the cap 40 from the outlet hub 28 opens the catheter system and exposes an introducer tip 44. The distal tip 34 of the catheter preferably resides just inside the introducer tip 44 when packaged. The outlet hub 28 also may house a lubricating gel reservoir 46 and a catheter feed lock 48, both shown schematically. Prior to exiting the sheath 22, the catheter 24 passes through these components and is suitably lubricated for insertion into the urethra.

The feed lock 48 functions to permit one-way forward advancement of the catheter 24, but inhibits rearward movement thereof. Exemplary feed locks are disclosed in co-pending U.S. Patent Publication No. US 2019/0046766, the contents of which are hereby expressly incorporated by reference. It should be noted that rather than providing the lubricating gel reservoir 46, the catheter 24 may be pre-lubricated along its length, or may be provided with a dry hydrophilic coating which, when wetted, becomes lubricious. In the latter case, a small sachet of water is provided within the sheath 22 which, when ruptured, wets the catheter 24.

At the rear end of the system 20, an exemplary fluid valve has a housing 50 with a drain 52 on an outlet end, a shaft stub (not shown) over which the rear end of the sheath 22 seals, such as with the stricture 33, and an actuator 56 which opens and closes the valve. The illustrated embodiment shows a simple piston/cylinder type of valve with a plunger-type of actuator 56 that moves linearly through the tubular housing to alternately occlude and open an internal throughbore between the drain 52 and shaft stub. As shown, the plunger actuator 56 is partially retracted out of the housing 50 to close the valve and maintain the inner contents of the sheath 22 sterile. Of course, other such fluid valves are contemplated, such as a stopcock, pinch valve, slider type of actuator, etc.

In use, after removal of the cap 40 and prior to longitudinal advancement of the catheter 24 from the sheath 22, the user inserts the introducer tip 44 into the urethra (men or women). The user then advances the catheter 24 forward, as indicated by the arrow in FIG. 1B, by pinching it through the relatively flexible sheath 22 and urging it forward while holding the outlet hub 28 steady. The introducer tip 44 is sized to fit within the outer end of the urethra and made of a flexible elastomer which has petals that the catheter tip 34 spreads apart upon passage therethrough. The introducer tip 44 helps prevent any bacteria that may be around the urethra opening from contacting the catheter tip 34, which in turn helps reduce instances of infection.

Eased by the lubricated nature of the catheter 24, the user continues to slowly push the catheter 24 through the introducer tip 44 and into the urethra until the catheter reaches the bladder and urine begins to flow. The catheter 24 has one or more small eyelets (not shown) at its distal tip 34 into which the urine flows. The enlarged funnel 36 prevents complete extraction of the catheter 24 from within the sheath 22 as it abuts the internal components of the forward hub 28. Urine flows through the funnel 36 into the inner cavity of the sheath 22.

Figure 3:
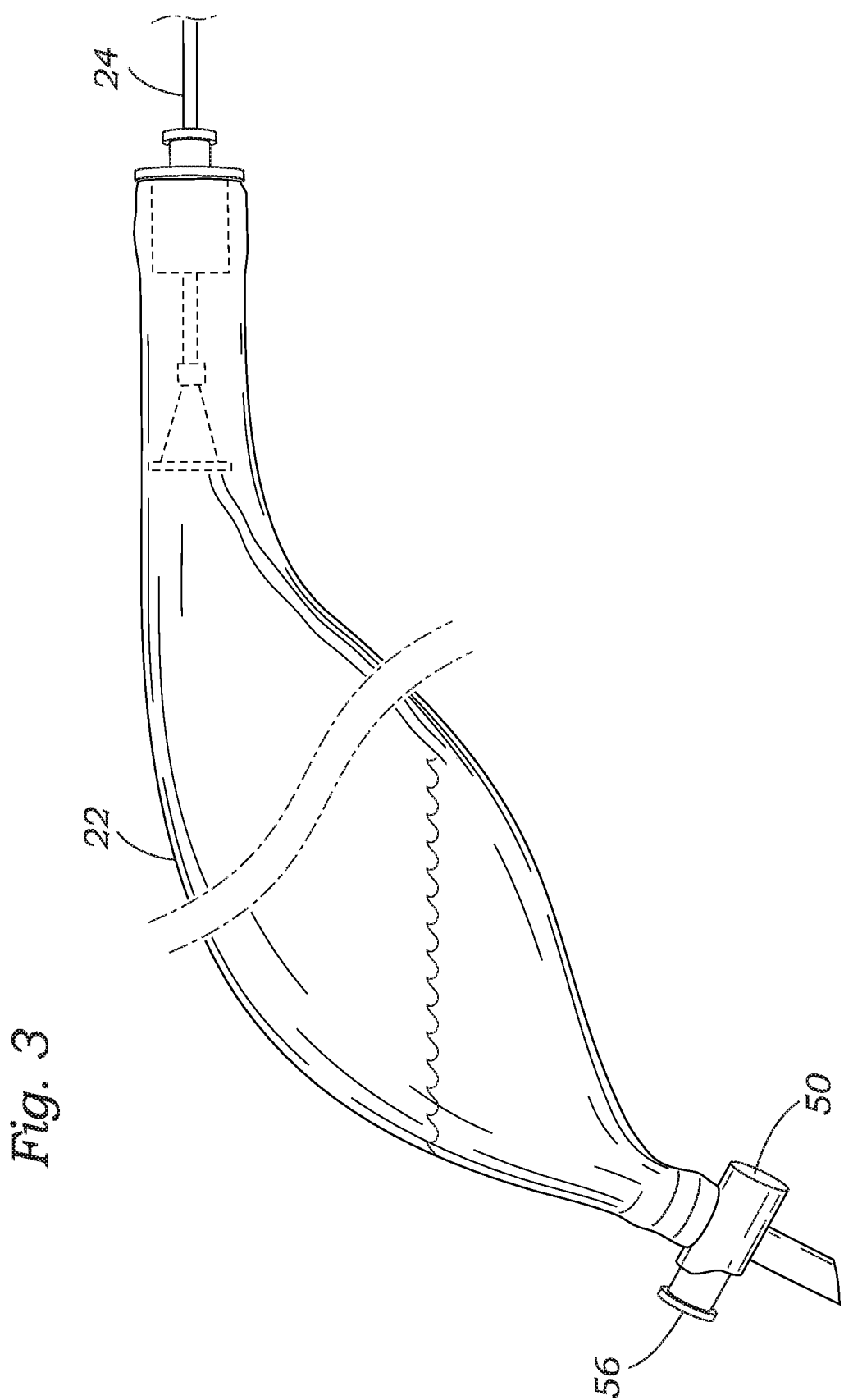
FIG. 3 is an isolated view of the system of the present application being used as a closed system with a collection bag.

FIGS. 2 and 3 are views of the catheter system 20 illustrating two options for use thereof—FIG. 2 as a drain line into a toilet, and FIG. 3 as a collection bag. In both uses, the sheath 22 is extended so that it is relatively smooth and forms either an uninterrupted flow channel or a pouch-like bag or receptacle. FIGS. 1B and 2 show the catheter 24 nearly fully withdrawn out of the sheath 22 while the sheath is extended to a full longitudinal dimension L of anywhere from 24-45 inches. In a preferred embodiment, the dimension of the extended sheath 22 is between about 1.5-2.0 times longer than the length $\ell$ of the catheter 24, or alternatively, the length $\ell$ of the catheter 24 is between about ½ to ⅔ the dimension L of the extended sheath 22. For example, the length $\ell$ of the catheter 24 is between about 12-16 inches if the sheath 22 has an extended dimension L of 24 inches, and between about 22-30 inches if the sheath 22 has an extended dimension L of 45 inches, with all the various combinations in between. The catheter length $\ell$ is thus between about 12-30 inches.

In FIG. 2, the valve actuator 56 has been depressed as indicated to open the fluid valve. Although not shown, the user holds the outlet hub 28 against the external opening of the urethra with the catheter 24 inserted, such as while seated on the toilet or in an adjacent seat or wheelchair. (It should be understood that the proportional size of the system 20 is somewhat enlarged for clarity.) The weight of the valve also assists to keep the drain line inserted into a toilet bowl or other receptacle. The user continues to drain urine until the flow stops, and then closes the valve. Retraction of the catheter 24 from the urethra and then into the sheath 22 provides a neat and convenient disposable product.

FIG. 3 shows the valve closed with the plunger-actuator 56 once again retracted. In this configuration, the user may initiate urine flow into the inner cavity of the sheath 22, which forms a pouch-like receptacle or collection bag. When done, the user may simply retract the catheter back into the sheath 22 and store the clean assembly until an appropriate moment to drain the urine by opening the valve. In a preferred embodiment, the length L and diameter of the sheath 22 are such that the inner volume is between about 600-2000 ml, sufficient to hold most urinary discharges.

Figure 4A:
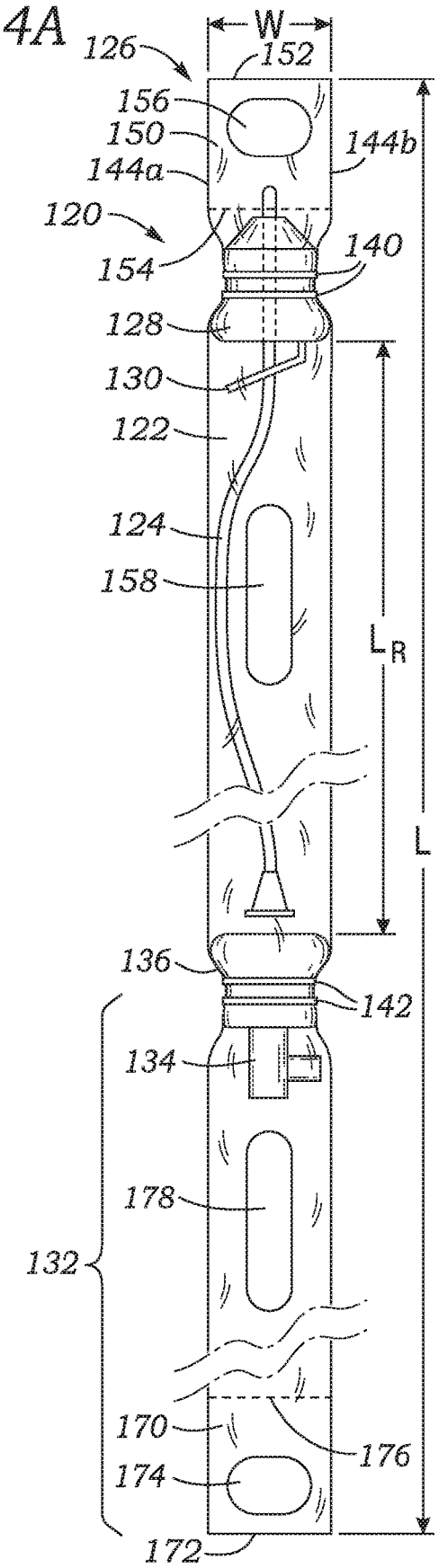
FIG. 4A is an elevational view of a further exemplary catheter system with an outer sheath longitudinally extended and the catheter housed therein.

FIG. 4A is an elevational view of a further exemplary catheter system 120 having an elongated flexible outer sheath 122 longitudinally extended. A catheter 124 is housed in an inner cavity within the sheath 122 and arranged to be advanced out of a rigid outlet hub 128 adjacent a forward end 126 of the system 120.

The rigid outlet hub 128 may be configured in a similar manner as the outlet hub 28 described above, and in particular preferably includes a movement control valve 130. The movement control valve 130 may be configured as an angled flap with a hole therethrough. Various such movement control valves 130 are disclosed in U.S. Patent Publication No. 2019/0282782 to Palmer, which is expressly incorporated herein.

As the catheter 124 advances distally through the hub 128, the flap flexes so as to be perpendicular to the catheter, which permits relative movement. However, if the catheter 124 is displaced in the opposite direction, proximally, the flap flexes to the angled configuration shown which impedes relative movement of the catheter. This serves to enable the user to displace the catheter 124 forward in increments with the movement control valve 130 preventing catheter retraction between incremental movements.

In addition to a movement control valve, the outlet had 128 may also house a lubricating gel reservoir, the catheter 124 may be pre-lubricated along its length, or may be provided with a dry hydrophilic coating which, when wetted, becomes lubricious. In the latter case, a small sachet of water may be provided within the sheath 122 which, when ruptured, wets the catheter 124.

A rearward end 132 of the system 120 houses a drain valve 134. The drain valve 134 may be as described above, and preferably is mounted within a rigid housing 136. The outer sheath 122 surrounds the rigid housing 136 and is desirably bonded thereto using heat welds, adhesives, or the like, shown as two bond lines 140. Likewise, the rigid outlet hub 128 is received within the outer sheath 122 and secured thereto at bond lines 142, which again may be heat welds, adhesives, or the like. In this manner, a sealed inner volume is formed within the outer sheath 122 between the outlet hub 128 and housing 136 of the drain valve 134. This sealed inner volume comprises a reservoir for urine should the system 120 be used as a collection bag.

Figure 4B:
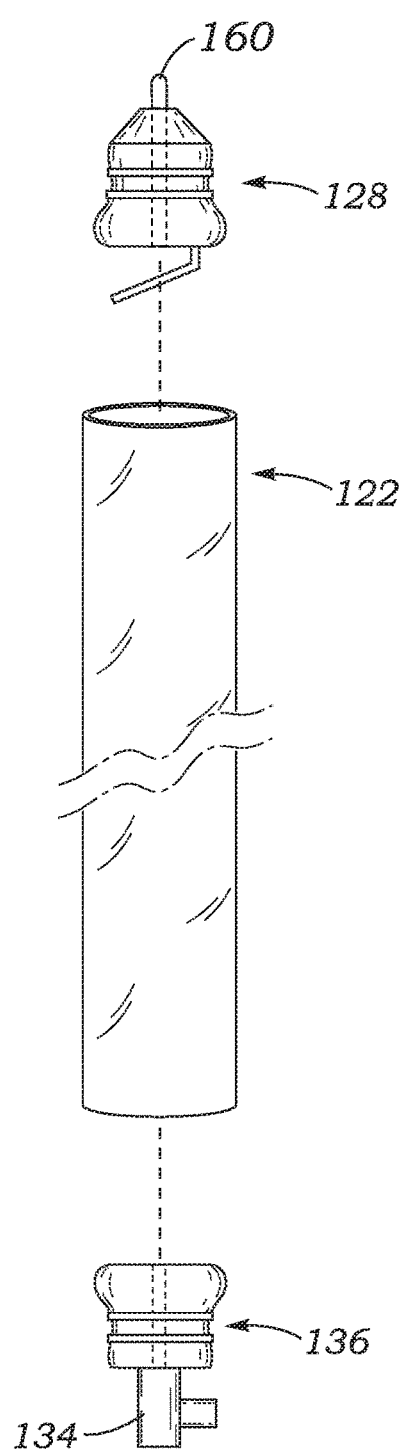
FIG. 4B is an exploded view of the components of the catheter system.

FIG. 4B is an exploded view of the components of the catheter system 120. For ease of manufacturing, the system includes three components: the outer sheath 122, the outlet hub 128, and the rigid housing 136 of the drain valve 134. These components are desirably formed of polymeric materials, such as described above. More particularly, the outer sheath 122 may be formed of a polyethylene or polyurethane film, or the like, while the hub 128 and housing 136 are formed of a like polymer. This enables the outer sheath 122 to be easily heat bonded to the exterior of the hub 128 and housing 136.

With reference back to FIG. 4A, the outer sheath 122 includes a number of features that are formed by heat sealing its edges or opposite panels together. In particular, the outer sheath 122 is initially a tube, such as seen in FIG. 4B. Of course, the tube as shown may be extruded as such or may be formed from a flat sheet that is joined at a longitudinal seam line. Regardless of how the outer sheath 122 is initially formed, it may be pressed flat such that it has to opposite longitudinal and parallel edges 144a, 144b. The overall shape of the flattened outer sheath 122 is an elongated rectangle with a length dimension L and a width dimension W, as shown. A shorter length $L_R$ is also indicated between the outlet hub 128 and housing 136 of the drain valve 134 indicating the portion of the inner cavity used as a reservoir for urine should the system 120 be used as a collection bag.

The width dimension W equals one half of the circumference of the tubular form of the outer sheath 122, seen in FIG. 4B, such that the following equations apply:

$2 \times W = \pi \times D = C$, where $D$ is the diameter of the tube and $C$ the circumference, and $V = \pi r^2 \times L_R = W^2/\pi \times L_R$, where $V$ is the volume of the reservoir for urine.

In a preferred embodiment, the outer sheath 122 has a diameter D of between 1-2 inches (2.54-5.08 cm), and an initial or extended length L of between 24-45 inches (61-114 cm). Moreover, the length of the catheter 124 is desirably between about 12-30 inches (30.5-76.2 cm). The shorter length $L_R$ of the reservoir is desirably also between about 12-30 inches (30.5-76.2 cm) to accommodate the full length of the catheter 124 without having to curl or otherwise bend the catheter within the elongated sheath 122. Consequently, the volume V of the portion of the inner cavity available as a reservoir for urine is between about 0.061-0.101 L for thinner sheaths having a diameter of 1 inch, and 0.243-0.405 L for wider sheaths having a diameter of 2 inches. Of course, the length and width of the sheath 122 can vary, and may be larger than 2 inches. Preferably, the volume V of the reservoir for urine is somewhere between 0.061-0.5 L, which equates to about 2-68 fluid ounces. Of course, it is unlikely that someone will use a short thin catheter system 120 as a reservoir since the volume will be relatively small. In that case, the dual-mode catheter system 120 will more likely be used as a drainage tube, as will be explained.

With reference again to FIG. 4A, the outer sheath 122 in the final system 120 has a forward segment 150 extending a short distance past the outlet hub 128. The longitudinal and parallel edges 144a, 144b continue along the forward segment 150, and terminate at a lateral edge 152. There is thus a generally rectangular portion of the outer sheath 122 extending past and adjacent to the outlet hub 128. Each of the edges 144a, 144b, 152 is sealed, while the opposite panels of the outer sheath 122 are not attached therebetween and form a volume therein.

A line of weakness or score line 154 extends laterally across the forward segment 150 immediately adjacent to the outlet hub 128. Furthermore, a finger hole 156 is formed in a midportion of the forward segment 150, typically by heat sealing in the pattern of the hole and then cutting or stamping out the material circumscribed thereby. A second finger hole 158 is similarly formed in a midportion of the outer sheath 122 in the rectangular region between the outlet hub 128 and the housing 136 of the drain valve 134. A user may easily separate the forward segment 150 from the remainder of the outer sheath 122 by grasping the finger hole 156 in one hand and either the outlet hub 128 or second finger hole 158 and pulling. The score line 154 easily severs, resulting in exposure of the forward or distal end of the outlet hub 128.

In this manner, the user can easily prepare the catheter system 120 for use. That is, the user inserts an introducer tip 160 into the urethra (men or women) and advances the catheter 124 forward by pinching it through the relatively flexible sheath 122 and urging it forward while holding the outlet hub 128 steady. Without any other preparation, the system 120 can thus be used as a collection bag. Another advantage is that the drain valve gives better control than just a tear open spot on the bag with less splashing and misdirected urine.

In a second mode of operation, the catheter system 120 can be used as a drain line. The outer sheath 122 includes an elongated rearward segment 170 adjacent to the housing 136 and drain valve 134. Again, longitudinal and parallel edges 144*a*, 144*b* continue along the rearward segment 170, and terminate at a lateral edge 172. A finger hole 174 is formed adjacent the lateral edge 172, and a lateral line of weakness or score line 176 provided toward the housing 136. A second finger hole 178 is again provided in the outer sheath 122 between the housing 136 and score line 176. By grasping the finger hole 174 and pulling, while also holding either the housing 136 or second finger hole 178, a user can easily detach a portion of the rearward segment 170, thus opening the inner cavity of the outer sheath 122 and exposing the drain valve 134.

The extended length L of the outer sheath 122 is sufficiently long so as to extend from the outlet hub 128 held by a user while seated adjacent and not on a toilet to the severed rearward segment 170 suspended over the toilet. By manipulating the drain valve 134 to the open position, a user can then directly urinate into the toilet. Oftentimes, the length of the outer sheath 122 is long enough such that the drain valve 134 is also positioned over the toilet, in which case the weight of the valve helps to keep the rearward end within the toilet.

It should be understood that the catheter system 120 can also the utilized both as a collection bag and has a drain line. That is, the drain valve 134 can remain closed while the user advances the catheter 124 and urinates, thus filling the reservoir volume between the outlet hub 128 and the housing 136. Once finished, the user typically retracts the catheter 124 from the body and disposes of the entire system with the urine in a trash receptacle. However, in cases where a toilet or other waste receptacle is readily accessible, the user can instead position the open rearward segment 170 of the outer sheath 122 and open the drain valve 134 to empty the contents of the system. That is, the system 120 thus functions as a temporary collection bag just long enough for the user to empty the reservoir into the toilet. This may be preferable, for example, where the user has limited dexterity and has a hard time draining the system in the toilet while urinating, and must perform the task in two steps. Subsequently, the empty system 120 is disposed of in a trash receptacle.

FIG. 5A is a perspective view of the catheter system of FIG. 4A folded in half, and FIG. 5B is an elevational view with the two folded halves flat against one another. As mentioned, the total length L is between about 24-114 inches (61-114 cm) so that the system 120 can be used as a real-time drain line if the toilet. However, such a length is relatively cumbersome to carry around. Typically, a user of such products carries several of them on their person so that they have a supply if needed.

As seen in FIG. 5A, the system 120 can be folded at its midpoint as indicated at 180. By juxtaposing the two halves of the system, as seen in FIG. 5B, the forward and rearward segments 150, 170 are aligned with each other, which also aligns the two score lines 154, 176. The half-length system can then be folded again along its centerline C/L at fold 182 as indicated in FIG. 6A. During this folding the system may be also twisted 180 degrees to prevent catheter tubing kinking, which keeps the tube bends in a more gentle radius to prevent kinks.

FIG. 6B is an elevational view of the assembled twice folded catheter system 120 with a sleeve-like shipping seal 190 provided to prevent the system from unfolding before it is needed. The shipping seal 190 preferably has printing thereon indicating the type of system, the manufacturer, and instructions for use.

To utilize the system 120, the user removes the shipping seal 190 and unfolds the system once into the configuration of FIG. 5B. At this point, both of the forward and rearward segments 150, 170 can be removed together by tearing the score lines 154, 176. This is a convenient way to open both ends of the system for use as a drain line. The system 120 is then unfolded once more into its full length.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A dual-purpose urinary catheter system, comprising:
    a flexible outer tubular sheath having an extended length L and a significantly smaller lateral width W when flat, an inner cavity, a forward end and a rearward end, wherein the outer sheath is a thin polymer tube that may be folded longitudinally at lateral fold lines to a folded length and is configured to extend longitudinally to the extended length L by straightening out the fold lines;
    a urinary catheter disposed within the inner cavity of the outer sheath, the catheter having a front end and a length l, wherein the length l of the catheter is shorter than the extended length L of the outer sheath;
    an outlet hub secured within the outer sheath adjacent the forward end, the outlet hub defining a throughbore sized to permit extraction of the catheter front end; and
    a valve secured within the outer sheath adjacent the rearward end, wherein the valve may be either closed or opened to permit fluid flow therethrough;
    wherein when extended longitudinally to the extended length L the catheter system may function as a collection bag when the valve is closed and a drain line when the valve is open, and wherein
    the extended length L is sufficiently long so as to extend from the outlet hub held by a user while seated adjacent and not on a toilet to the valve suspended over the toilet, the weight of the valve helping to keep the valve over the toilet.

2. The dual-purpose urinary catheter system of claim 1, wherein the outer sheath extends beyond the outlet hub in a forward segment to the forward end and is sealed to maintain sterility of the outlet hub, and wherein the outer sheath has a lateral line of weakness or score line between the outlet hub and the forward end which permits removal of the forward segment to expose the outlet hub.

3. The dual-purpose urinary catheter system of claim 2, wherein the outer sheath extends in a rearward segment beyond the valve to the rearward end and is sealed to maintain sterility of the valve, and wherein the outer sheath has a lateral line of weakness or score line between the valve and the rearward end which permits removal of the rearward segment to expose the valve.

4. The dual-purpose urinary catheter system of claim 3, wherein both the forward segment and the rearward segment have finger holes formed therein to facilitate their removal at the respective lateral lines of weakness or score lines.

5. The dual-purpose urinary catheter system of claim 1, wherein the catheter length l is between about 12-30 inches.

6. The dual-purpose urinary catheter system of claim 1, wherein the inner cavity has a volume of between about 0.061-0.5 L.

7. The dual-purpose urinary catheter system of claim 1, wherein the valve has a plunger actuator that moves linearly through a tubular housing to alternately occlude and open an internal throughbore in the valve.

8. The dual-purpose urinary catheter system of claim 1, wherein the outlet hub further houses a feed lock through which the catheter passes and permits forward advancement of the catheter but inhibits rearward movement thereof.

9. The dual-purpose urinary catheter system of claim 1, wherein the outlet hub further houses a lubricant chamber therein to lubricate the catheter as it passes therethrough.

10. A dual-purpose urinary catheter system, comprising:
a flexible outer tubular sheath having an extended length L and a significantly smaller lateral width W when flat, an inner cavity, a forward end and a rearward end, wherein the outer sheath is a thin polymer tube that may be folded longitudinally at lateral fold lines to a folded length and is configured to extend longitudinally to the extended length L by straightening out the fold lines;
a urinary catheter disposed within the inner cavity of the outer sheath, the catheter having a front end and a length l, wherein the length l of the catheter is shorter than the extended length L of the outer sheath; and
an outlet hub secured within the outer sheath adjacent the forward end, the outlet hub defining a throughbore sized to permit extraction of the catheter front end; and
a valve secured within the outer sheath adjacent the rearward end, wherein the valve may be either closed or opened to permit fluid flow therethrough, wherein the catheter system may function as a drain line when the valve is open;
wherein the outer sheath extends in a rearward segment to the rearward end and is sealed, and wherein the outer sheath has a lateral line of weakness or score line in the rearward segment which permits removal of the rearward segment,
wherein when extended longitudinally to the extended length L the catheter system may function as a collection bag when the rearward segment is left intact or a drain line when the rearward segment is removed.

11. The dual-purpose urinary catheter system of claim 10, wherein the rearward segment has a finger hole formed therein to facilitate removal thereof at the lateral line of weakness or score lines.

12. The dual-purpose urinary catheter system of claim 10, wherein the outer sheath extends beyond the outlet hub in a forward segment to the forward end and is sealed to maintain sterility of the outlet hub, and wherein the outer sheath has a lateral line of weakness or score line between the outlet hub and the forward end which permits removal of the forward segment to expose the outlet hub.

13. The dual-purpose urinary catheter system of claim 12, wherein both the forward segment and the rearward segment have finger holes formed therein to facilitate their removal at the respective lateral lines of weakness or score lines.

14. The dual-purpose urinary catheter system of claim 10, wherein the outer sheath is folded twice longitudinally at lateral fold lines to a folded length that is about one quarter of the extended length L, and further including a sleeve-like shipping seal provided around the folded system to prevent the system from unfolding, the shipping seal having printing thereon with product information.

15. The dual-purpose urinary catheter system of claim 10, wherein the extended length L is sufficiently long so as to extend from the outlet hub to the valve suspended over the toilet when the outlet hub is held by a user seated adjacent and not on a toilet.

16. The dual-purpose urinary catheter system of claim 10, further including a sleeve-like shipping seal provided around the folded system to prevent the system from unfolding, the shipping seal having printing thereon with product information.

17. The dual-purpose urinary catheter system of claim 10, wherein the valve has a plunger actuator that moves linearly through a tubular housing to alternately occlude and open an internal throughbore in the valve.

18. The dual-purpose urinary catheter system of claim 10, wherein the catheter length l is between about 12-30 inches and the inner cavity has a volume of between about 0.061-0.5 L.

19. The dual-purpose urinary catheter system of claim 10, wherein the outlet hub further houses a feed lock through which the catheter passes and permits forward advancement of the catheter but inhibits rearward movement thereof.

20. The dual-purpose urinary catheter system of claim 10, wherein the outlet hub further houses a lubricant chamber therein to lubricate the catheter as it passes therethrough.

* * * * *